United States Patent [19]

Thomas et al.

[11] Patent Number: 5,103,179

[45] Date of Patent: Apr. 7, 1992

[54] WATER ANALYZER WITH MULTIPLE ELECTRODES

[75] Inventors: Frank A. Thomas; Kenneth J. Evers; Richard T. Westlake, all of Hillsboro, Oreg.

[73] Assignee: Industrial Chemical Measurement, Inc., Hillsboro, Oreg.

[21] Appl. No.: 489,444

[22] Filed: Mar. 5, 1990

[51] Int. Cl.⁵ .............................................. G01N 27/27
[52] U.S. Cl. ................................... 324/438; 324/439; 324/441; 204/412; 204/415; 204/420
[58] Field of Search ..................... 324/438, 441, 439; 204/402, 412, 415, 420

[56] References Cited

U.S. PATENT DOCUMENTS

| | | | |
|---|---|---|---|
| 4,039,933 | 8/1977 | Moran | 324/425 |
| 4,691,167 | 9/1987 | Vlekkert et al. | 324/438 |
| 4,912,417 | 3/1990 | Gibboney et al. | 324/438 |
| 4,940,946 | 7/1990 | Nazaryan | 324/438 |
| 4,998,068 | 3/1991 | McKee, Jr. | 324/438 |

Primary Examiner—Jack B. Harvey
Assistant Examiner—Glenn W. Brown
Attorney, Agent, or Firm—Edgar W. Averill, Jr.

[57] ABSTRACT

A water analyzer having several electrodes of the type which normally interfere with one another. These electrodes include a first electrode which is an active measurement electrode which perturbs the solution in which it is used and a second electrode whose reading is affected by the operation of the first electrode. Accurate readings are provided by sequencing the operation of the electrodes so that they are not always operating at the same time. In addition, further correction of the readings is provided to compensate for the known error resulting from the operation of the active electrode or electrodes. Such electrodes read conditions such as pH, dissolved oxygen and conductivity.

13 Claims, 2 Drawing Sheets

WATER ANALYZER WITH MULTIPLE ELECTRODES

BACKGROUND OF THE INVENTION

The field of the invention is chemical analysis of water solutions, liquids or gas analysis, and the invention relates more particularly to the use of multiple electrodes on a single probe so that several readings may be made at a single immersion.

Electrode measurements in solution can be grouped into two general classes, namely, active measurements and passive measurements. Passive measurements are those in which the measurement process does not perturb the solution. Examples of passive measurements include the measurement of temperature, pH, the measurement of the reference potential of a solution and the measurement of an ion selective electrode potential. Active measurements result in some external perturbation of the solution to carry out the measurement. This is generally applied by some portion of the measurement sensor. Examples of active measurements include the measurement of conductivity, the measurement of dissolved oxygen and the measurement of dissolved carbon dioxide.

The use of combination electrodes such as pH and reference potential or oxidation reduction potential and reference potential has long been known to simplify design problems. These combination electrodes ease cabling problems and reduce the amount of sample required for a measurement. In the past, combination electrodes have either been exclusively passive sensors or have been used to measure only a single parameter at a time. It was believed that the interference of the reading of one sensor by the operation of another precluded the grouping of such interfering sensors.

SUMMARY OF THE INVENTION

It is an object of the present invention to provide a water analyzer having a probe with a plurality of interfering sensors.

The present invention is for a water analyzer having a plurality of electrodes for measuring a plurality of conditions including electrodes which interfere with one another. The analyzer has a first electrode of the type which uses an active measurement which perturbs the solution in which it is used when it is energized. A second electrode is of the type which is affected by the operation of the first electrode, and the second electrode is positioned at a fixed relationship with respect to the first electrode. Sequencing means are provided which activate the first electrode at a different time than the second electrode. A further correction is also disclosed which includes a microprocessor which corrects the sensor input for the known affect of the interfering sensor to provide an accurate reading. Preferably, the sensors include dissolved oxygen, pH and conductivity sensors.

DESCRIPTION OF THE PREFERRED EMBODIMENTS

Figure 1:
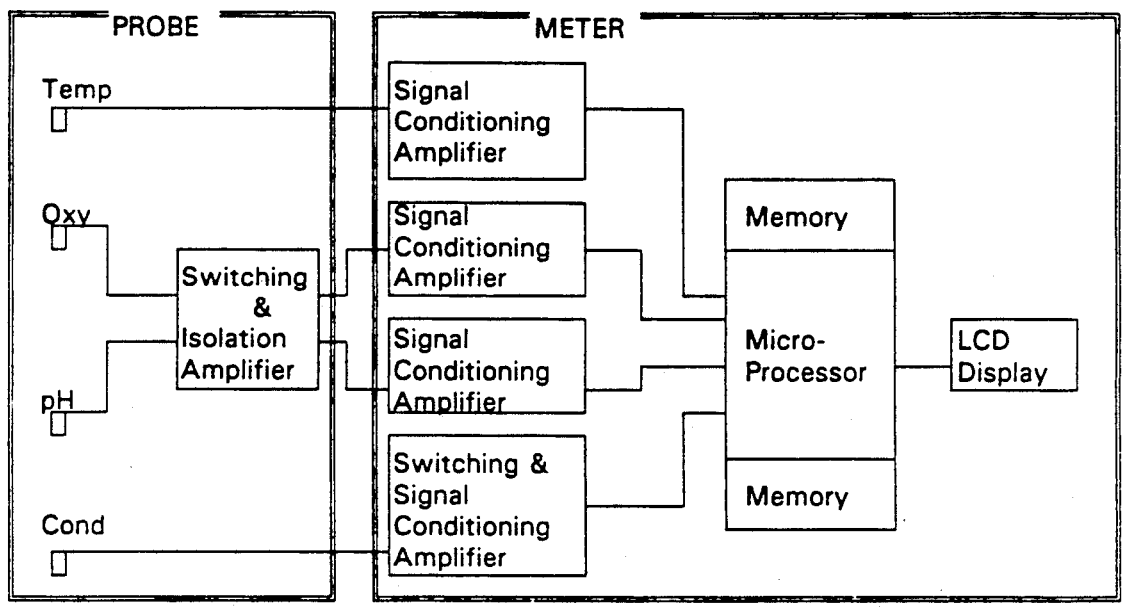
FIG. 1 is a diagrammatic view showing the elements of the probe and meter of the present invention.
Figure 4:
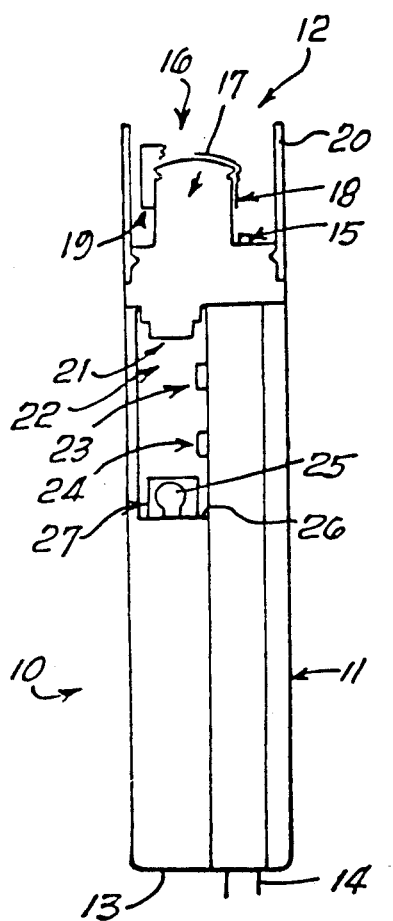
FIG. 4 is an enlarged side view, partially broken away, of the probe of FIG. 3.

The present invention provides means for allowing a variety of both active and passive sensors to be used for the simultaneous display of all their response values. To accomplish this, it is necessary to group the desired sensors or electrodes. These include pH electrodes, reference potential electrodes, temperature sensors, oxidation reduction potential electrodes, ion selective electrodes, conductivity electrodes, oxygen electrodes, hydrocarbon sensors, carbon dioxide sensors or any combination of these. One preferred grouping is shown in FIG. 1 where a temperature sensor, a dissolved oxygen electrode identified by the letters "Oxy," a pH sensor and a pair of conductivity sensors are used. These sensors are shown in FIG. 4 where the probe is indicated generally by reference character 10. Probe 10 has an elongated, generally rectangular body 11 with an upper end indicated generally at 12 and a lower end 13 from which a cable 14 having a plurality of conductors therein exits probe 10.

Probe 10 includes a temperature sensor 15 near the upper end 12. A dissolved oxygen sensor 16 includes a gold cathode 17 covered with a membrane 18. An electrode filling solution such as 1.5 M potassium chloride is placed between membrane 18 and gold cathode 17 in a manner known to those familiar with dissolved oxygen sensor. The membrane 18 is held over the gold cathode by membrane retaining ring 19. A protective ring, or guard, 20 is snapped over the upper end 12 of probe 10 to protect the membrane 18 and gold cathode 17 from damage. An oxygen diaphragm 21 is positioned in an opening 22 formed near the center of probe 10. The oxygen diaphragm is more elastic than the membrane and is used to prevent changes in pressure from distorting the oxygen membrane. It is also used to help evacuate air bubbles when filling the sensor chamber.

A pair of conductivity electrodes 23 and 24 are positioned within opening 22. A pH probe 25 is held at the base 26 of opening 22 and is typically covered with a protective cap 27 when not in use. Protective cap 27 is filled with a solution such as 10% potassium chloride in a pH4 buffer.

Figure 3:
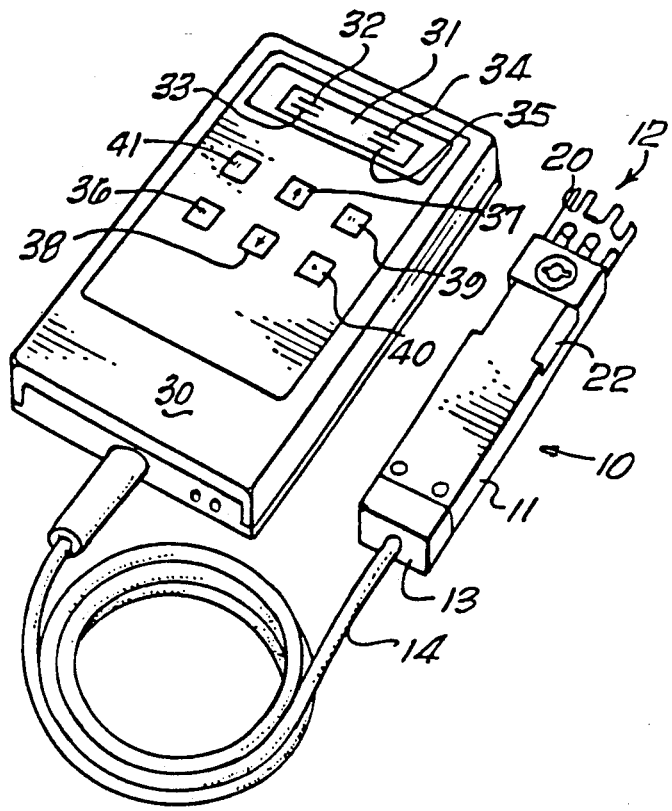
FIG. 3 is a perspective view of the external portions of the probe and meter of FIG. 1.

Probe 10 is shown in perspective view in FIG. 3 where it can be seen that cable 14 provides sufficient length (such as six feet) so that the probe can be immersed in the solution to be tested while the meter is held by hand. Meter 30 has a digital readout window 31 which has areas 32, 33, 34 and 35 for the simultaneous display of the corrected readings for temperature (32), conductivity (33), pH (34), and dissolved oxygen (35) in ppm.

The meter also includes an on/off switch 36, switches to scroll up or down through the menu 37, 38, switches to enter 39 and store 40 values and a switch 41 to select the operating mode.

In operation, probe 10 is immersed in a solution to be measured, and the meter is turned on. This begins a timing sequence, which is shown best in FIG. 2 of the drawings, wherein the temperature is immediately turned on as is the dissolved oxygen electrode. After three seconds, the dissolved oxygen electrode is turned off, and the pH probe is turned on. This condition lasts for about two seconds, after which the pH electrode is turned off, and the dissolved oxygen electrode is turned back on, and the conductivity electrode is turned on. After an additional three seconds, the conductivity electrode is turned off, and after about eight seconds, the temperature is sensed. The dissolved oxygen is read, and the conductivity is determined. The pH reading was taken at about five seconds, just before the pH electrode was de-energized. These values are then manipulated, as indicated in the diagram of FIG. 1, and fed into a microprocessor by way of appropriate amplifiers and switching means. The microprocessor is programmed to correct for the interaction of the electrodes.

Figure 2:
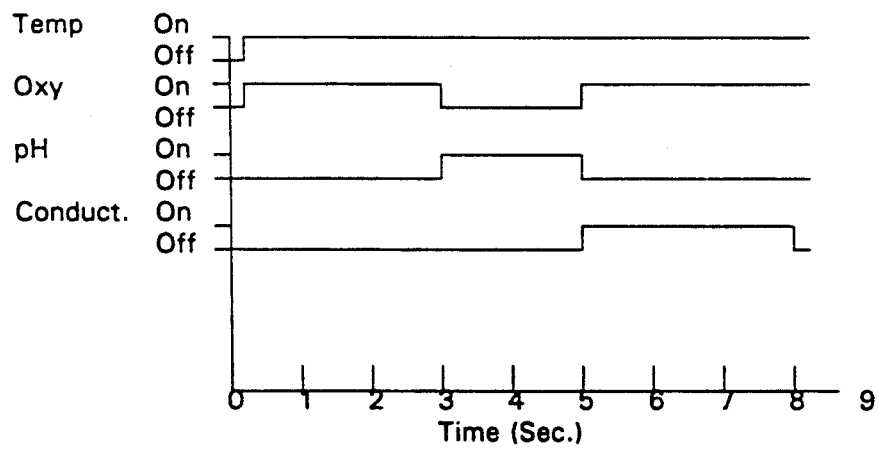
FIG. 2 is a graph showing the on and off configuration of the sensors of the probe of FIG. 1.

For instance, it is known that the dissolved oxygen electrode is an active electrode. That is, it perturbs the solution and affects the pH reading. This affect is compensated in the meter of the present invention in several ways. First, the oxygen and pH readings are done sequentially and not at the same time, that is, as shown best in FIG. 2, the oxygen sensor is turned off as the pH sensor is turned on. The pH sensor is then turned off before the oxygen sensor is again turned on. In the case of oxygen and pH, the affect or perturbing of the solution does not end instantaneously when the oxygen sensor is turned off. Therefore, it is necessary to further correct the pH reading for the affect of the oxygen sensor. This is done in the microprocessor, and the values which are entered into the microprocessor to make this correction are easily determined by making a series of measurements in solutions of a known pH and determining a factor to correct the pH based upon the observed error. By maintaining the constant configuration of electrode 10, this correction has been found to be a very accurate one particularly when combined with the timed sequencing as shown in FIG. 2. It is also possible with the combination electrode of the present invention to correct the pH reading for temperature and for conductivity. It is further possible to correct the conductivity reading for temperature and pH. Furthermore, the dissolved oxygen reading can be corrected for temperature, conductivity and pH.

The use of a combination probe further assures the accurate sampling of a single volume of tested solution as compared to that resulting from separate probes at different times. Also by the use of the meter of the present invention, the need for correction tables or curves is eliminated since this can be done within the meter.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

What is claimed is:

1. A water analyzer having a plurality of electrodes, including electrodes which interfere with one another, for measuring a plurality of conditions, said analyzer comprising:
  a first electrode of the type which uses an active measurement which perturbs the solution in which it is used when it is energized;
  a second electrode of the type whose reading is affected by the operation of the first electrode, said second electrode being positioned in a fixed relationship with respect to the first electrode; and
  sequencing means which activate said first electrode at a time different from the reading of said second electrode.

2. The water analyzer of claim 1 further including a digital data readout area and said water analyzer including memory means to display a plurality of readings simultaneously on said digital data readout area even though the readings are taken sequentially.

3. A water analyzer having a plurality of electrodes, including electrodes which interfere with one another, for measuring a plurality of conditions for a period of time even after such electrode has been de-energized, said analyzer comprising:
  a first electrode of the type which is an active measurement which perturbs the solution in which it is used when it is energized;
  a second electrode of the type whose reading is affected by the operation of the first electrode, said second electrode being positioned in a fixed relationship with respect to the first electrode;
  sequencing means which activate said first electrode at a time different from the reading of said second electrode; and
  preset correction means which correct the readings of said second electrode based upon its interaction with the first electrode.

4. The water analyzer of claim 3 wherein said preset correction means comprise a microprocessor including memory.

5. The water analyzer of claim 3 wherein said first electrode is a dissolved oxygen sensing electrode.

6. The water analyzer of claim 3 wherein said second electrode is a pH sensing electrode.

7. The water analyzer of claim 3 wherein said first electrode is a dissolved oxygen electrode, and said second electrode is a pH sensing electrode.

8. The water analyzer of claim 7 further including electronic temperature sensing means.

9. The water analyzer of claim 8 further including a pair of conductivity electrodes.

10. The water analyzer of claim 9 wherein said sequencing means first activates the temperature sensing means and the dissolved oxygen electrode, then, after a delay of at least one second, deactivates the dissolved oxygen electrode and, at about the same time, activates the pH electrode, then, after about one second, deactivates the pH electrode and activates the conductivity electrodes and the dissolved oxygen electrode, then, after about two seconds deactivates the conductivity electrodes and the reads the results of the dissolved oxygen electrode about eight seconds after its first activation.

11. The water analyzer of claim 10 wherein the results of the readings of the temperature sensing means and the four electrodes are fed into microprocessing means wherein the readings are corrected for the previously determined error caused by the interference among the electrodes.

12. The water analyzer of claim 11 wherein the reading of the dissolved oxygen electrode is corrected for the previously determined error caused by interference from the electrodes which read temperature, conductivity and pH.

13. The water analyzer of claim 12 wherein said water analyzer has a digital readout of temperature, dissolved oxygen, pH and conductivity which are read out simultaneously.

* * * * *